United States Patent

Gazza et al.

[11] Patent Number: 5,820,598
[45] Date of Patent: Oct. 13, 1998

[54] SYRINGE FOR THE INTRAMAMMARY ADMINISTRATION OF VETERINARY PHARMACOLOGICAL COMPOSITIONS

[75] Inventors: Carlo Gazza; Corrado Zaini, both of Ozzano Emilia, Italy

[73] Assignee: Fatro S.p.A., Bologna, Italy

[21] Appl. No.: 686,923

[22] Filed: Jul. 24, 1996

[30] Foreign Application Priority Data

Jul. 28, 1995 [IT] Italy .............................. MI95A1668 U

[51] Int. Cl.[6] ....................................................... A61M 5/00
[52] U.S. Cl. ........................ 604/117; 604/192; 604/275; 604/263
[58] Field of Search ................................... 604/192, 199, 604/200, 263, 275, 274, 68, 48, 54, 73, 93, 117, 181, 187, 239–243, 265, 905, 264

[56] References Cited

U.S. PATENT DOCUMENTS

| | | | |
|---|---|---|---|
| 4,850,970 | 7/1989 | Sutherland | 604/117 |
| 4,981,472 | 1/1991 | Ennis, III et al. | 604/117 |
| 4,986,818 | 1/1991 | Imbert et al. | 604/263 |
| 5,009,640 | 4/1991 | Pyret et al. | 604/117 |
| 5,053,020 | 10/1991 | Manchester | 604/275 |
| 5,059,172 | 10/1991 | Sutherland et al. | 604/117 |
| 5,135,496 | 8/1992 | Vetter et al. | 604/199 |
| 5,372,590 | 12/1994 | Haber et al. | 604/192 |
| 5,531,707 | 7/1996 | Kers et al. | 604/263 |

*Primary Examiner*—Ronald Stright, Jr.
*Attorney, Agent, or Firm*—Bucknam and Archer

[57] ABSTRACT

A syringe for the intramammary administration of veterinary pharmacological compositions, in particular for the treatment of bovine mastitis. The syringe comprises a container body (1), a cannula (3) extending axially from one of its ends, a removable shutter (4) surrounding the initial part of the cannula (3), and a protective cap (6) covering both the cannula (3) and the shutter (4). During use, when the cap (6) is removed, only the end part of the cannula (3) is freed so as to allow insertion into the initial section of the teat; when the shutter (4) is also removed, the entire cannula (3) is freed so as to allow insertion as far as the teat cistern.

2 Claims, 2 Drawing Sheets

SYRINGE FOR THE INTRAMAMMARY ADMINISTRATION OF VETERINARY PHARMACOLOGICAL COMPOSITIONS

FIELD OF THE INVENTION

The present invention relates to a syringe for the intramammary administration of veterinary pharmacological compositions, in particular for the treatment of bovine mastitis.

The treatment of bovine mastitis is a problem of considerable importance in dairy cows breeding.

The treatment method generally used consists of the administration of antibiotic compositions through the teat canal (intramammary administration).

For this type of administration plastic syringes with a single cannula of between 20 to 25 mm length are used.

This type of syringe has the disadvantage that it may transfer any pathogenic agents present inside the teat canal into the teat cistern and promote new infections or reduce the effectiveness of the treatment being performed.

Moreover, it has been scientifically demonstrated that the insertion of a long cannula may damage the layer of keratin present in the distal part of the teat which has the function of protecting the udder from bacterial infections.

Recently, syringes with a structure such that they are able to perform a dual function have been proposed: a first short cannula for insertion into the initial section of the teat and a longer cannula for total insertion, where required, as far as the cistern of the teat of a cow.

EP-B-0,454,676 describes a syringe of this type with a cannula of predetermined length covered by a double cap. The first innermost cap leaves only an end section of the cannula free, while the second outermost cap covers this end section of the cannula and is arranged partially over the inner cap.

During use, by removing only the outer cap, i.e. freeing only the tip section of the cannula, the latter may be inserted into the initial section of the teat, whereas if the inner cap is also removed, the cannula is completely freed and can be inserted as far as the teat cistern.

A syringe with this dual function is also described in EP-B-0,523,091. In this case the syringe has incorporated in it a small-length cannula for insertion into the initial section of the teat, onto which an extension covered by an outer cap is fitted.

Depending on whether only the outer protective cap or the cap and the cannula extension are removed, it is possible to have cannulas of different lengths for different uses: total insertion as far as the teat cistern or insertion only into the initial section of the teat.

The syringes described in the above-mentioned patents, although they provide the possibility for a double cannula length, are not very easy to handle and in particular are subject to the risk of contamination when used.

Another drawback of these syringes consists of their high construction and assembly cost, since different parts must be prepared and combined in order to obtain the complete syringe.

SUMMARY OF THE INVENTION

The object of the invention is to overcome the aforementioned drawbacks by providing a syringe for the intramammary administration of a veterinary pharmacological composition which has a simple and inexpensive construction, can be handled with very good ease and avoids entirely the risk of contamination during use.

Preferred embodiments of the invention are described in the sub-claims.

Substantially, the syringe according to the invention comprises a cylindrical body with a cannula of a predetermined length, covered partially from its base or tang by a tubular element acting as a shutter, in a protective cap.

Advantageously, the outer protective cap covers the entire cannula, including the shutter. Removal of this cap frees the distal end of the cannula, so as to allow insertion into the initial section of the teat. If the shutter is also removed, the entire cannula is freed so as to allow insertion as far as the teat cistern.

Preferably, the tubular shutter which partially covers the cannula is formed as one piece with the syringe and is connected to the tang of the cannula by means of a pre-breaking line which allows it to be separated by means of breakage.

BRIEF DESCRIPTION OF THE DRAWINGS

Further characteristic features of the invention will appear more clearly from the detailed description which follows, with reference, purely by way of example, to a non-limiting embodiment thereof, illustrated in the accompanying drawings, in which.

DESCRIPTION OF THE INVENTION

Figure 1:
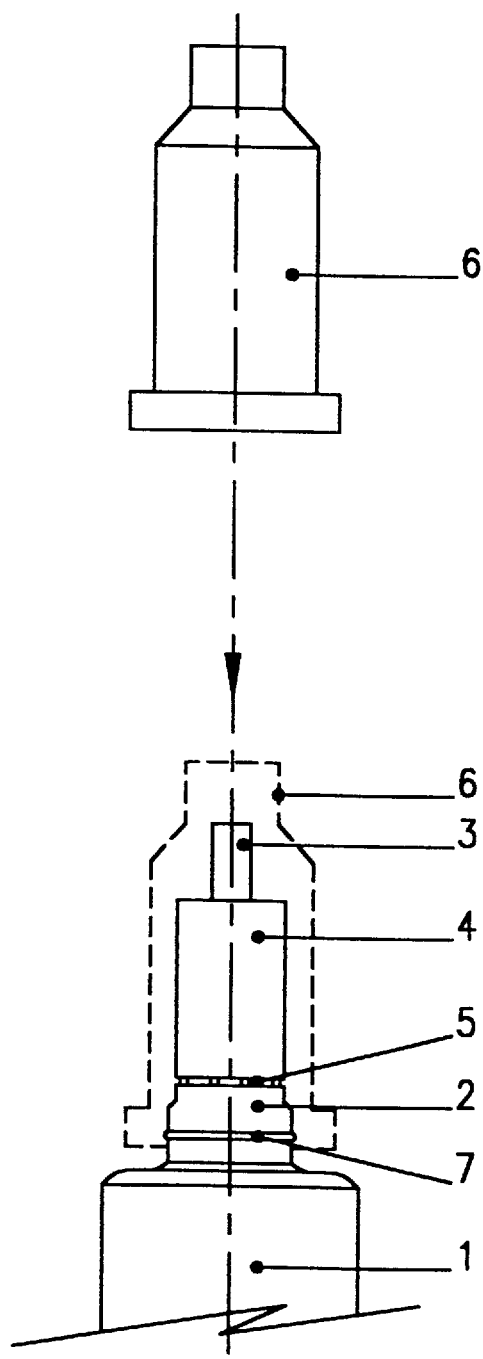
FIG. 1 is an elevation view of the syringe according to the invention, with the cap removed.
Figure 2:
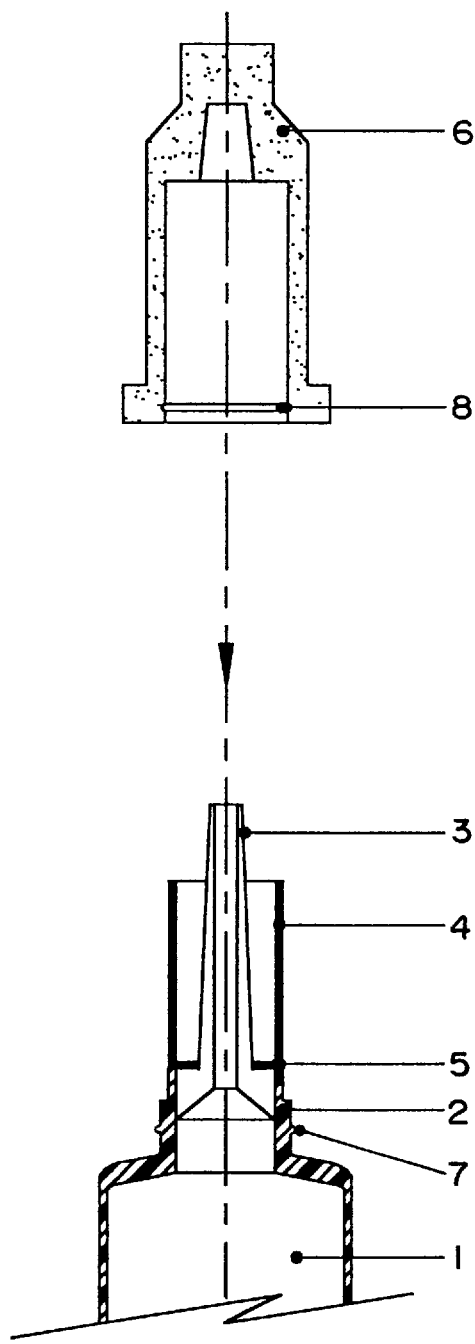
FIG. 2 is a cross sectional view of the syringe according to FIG. 1.

The syringe according to the invention comprises a cylindrical body 1, forming the reservoir of the syringe (shown only partially in the accompanying figures), and a cannula 3 which extends axially and is connected thereto by means of a cylindrical reducer or tang 2.

The bottom part of the cannula 3 is covered by a removable tubular sleeve 4 acting as a shutter. Advantageously, the shutter 4 is joined to the tang 2 by means of connection points 5 which allow separation by means of breakage following rotation of the shutter 4.

The syringe is completed by a protective cap 6 which sealingly covers the distal end of the cannula 3 and the tear-type shutter 4, as schematically shown by the broken line in FIG. 1.

In order to prevent the cap 6 from accidentally coming off the body 1 of the syringe, mutual engaging means may be provided, consisting, respectively, of an annular ridge 7 provided around the tang 2 of the syringe and a corresponding annular groove 8 formed inside the mouth of the cap 6.

All the components of the syringe are advantageously made of plastic material, preferably polyethylene. The cylindrical body 1 has a shape suitable for the intramammary administration of pharmaceutical compositions and a sufficient dimension for carrying out ordinary treatment with compositions for veterinary use.

As illustrated above, in the preferred embodiment of the invention, the cylindrical body 1, the tang 2, the cannula 3 and the shutter 4 form a single monolithic system made of plastic material which can be obtained with a single moulding operation.

This results in considerable savings as regards the mould, but in particular in terms of assembly of the various syringe components which in the case in question are reduced to only two, i.e. body-cannula-shutter and cap.

During the use of the syringe according to the invention, when the cap 6 is removed from it, only the distal end of the cannula 3 is freed so as to allow insertion into the initial section of the teat canal. On the other hand, when the shutter 4 is removed by means of breakage, the cannula 3 is freed over its entire length, providing the possibility of complete insertion of the cannula as far as the teat cistern.

Removal of the shutter 4 is performed in a particularly easy manner, ensuring total sterility of the cannula since the operator is prevented from touching it with his fingers and contaminating it.

From the above description the advantages of the syringe for intramammary treatment according to the invention are obvious.

We claim:

1. A syringe for the intramammary administration of veterinary pharmacological compositions, comprising a container body (1), said container body having two ends, a cannula (3) extending axially from one first end of said container body (1), said cannula having a bottom and a distal end, a tang (2) at said bottom, said tang connecting said cannula to said body, a shutter (4), said shutter covering said bottom of said cannula, connecting pieces (5), said connecting pieces joining said shutter to said tang, said body, said cannula, said tang and said shutter forming a monolithic structure and the syringe additionally comprises a cap (6), said cap covering said distal end of said cannula and said shutter, the syringe further comprising fastening means (7,8) for mutual fastening of said container body (1) and said cap (6).

2. The syringe according to claim 1, wherein said cap has a mouth, said mouth has an interior, said fastening means consist of an annular ridge (7) formed on said tang (2) and an annular groove (8) provided in said interior of said mouth of said cap (6).

* * * * *